United States Patent
Taboada et al.

(10) Patent No.: US 9,981,053 B2
(45) Date of Patent: May 29, 2018

(54) METHOD AND APPARATUS FOR RAPID STERILIZATION OF A ROOM

(71) Applicants: John Taboada, San Antonio, TX (US); John Martin Taboada, San Antonio, TX (US)

(72) Inventors: John Taboada, San Antonio, TX (US); John Martin Taboada, San Antonio, TX (US)

(*) Notice: Subject to any disclaimer, the term of this patent is extended or adjusted under 35 U.S.C. 154(b) by 0 days. days.

(21) Appl. No.: 15/805,110

(22) Filed: Nov. 6, 2017

(65) Prior Publication Data

US 2018/0071416 A1 Mar. 15, 2018

Related U.S. Application Data

(63) Continuation-in-part of application No. 15/489,705, filed on Apr. 17, 2017, now Pat. No. 9,808,546, which is a continuation-in-part of application No. 14/927,444, filed on Oct. 29, 2015, now Pat. No. 9,623,131.

(60) Provisional application No. 62/072,306, filed on Oct. 29, 2014.

(51) Int. Cl.
| | |
|---|---|
| *A61L 2/10* | (2006.01) |
| *A61L 2/24* | (2006.01) |
| *A61L 9/20* | (2006.01) |
| *A47L 11/40* | (2006.01) |
| *A61L 9/015* | (2006.01) |
| *H01J 61/02* | (2006.01) |

(52) U.S. Cl.
CPC ............ *A61L 2/10* (2013.01); *A47L 11/405* (2013.01); *A61L 2/24* (2013.01); *A61L 9/015* (2013.01); *A61L 9/20* (2013.01); *A61L 2202/11* (2013.01); *A61L 2202/14* (2013.01); *A61L 2202/25* (2013.01); *H01J 61/025* (2013.01)

(58) Field of Classification Search
USPC ....................................... 250/455.11, 454.11
See application file for complete search history.

(56) References Cited

U.S. PATENT DOCUMENTS

| | | | |
|---|---|---|---|
| 9,093,258 B2 | 7/2015 | Stibich et al. | |
| 9,165,756 B2 | 10/2015 | Stibich et al. | |
| 9,517,284 B1 | 12/2016 | Stibich et al. | |
| 2017/0312379 A1* | 11/2017 | Stibich | ...................... A61L 2/24 |

* cited by examiner

*Primary Examiner* — Kiet T Nguyen
(74) *Attorney, Agent, or Firm* — Taboada Law Firm, PLLC; John M. Taboada

(57) ABSTRACT

Methods and systems for sterilizing a room are disclosed, including using a laser to generate a pulsed laser beam; using a robotic arm to direct the pulsed laser beam to a scattering optical element and to change the position of the scattering optical element; and using the scattering optical element to substantially isotropically scatter the radiation of the pulsed laser beam to sterilize the room. The scattering optical element comprises a hollow fused silica bulb filled with solid fused silica spheres or a fiber optic bundle and in some embodiments the scattering optical element is rotated. The pulsed laser beam comprises a wavelength ranging between about 200 nm to about 320 nm and in some embodiments comprises nanosecond or picosecond light pulses. Other embodiments are described and claimed.

20 Claims, 4 Drawing Sheets

METHOD AND APPARATUS FOR RAPID STERILIZATION OF A ROOM

I. CROSS REFERENCE TO RELATED APPLICATIONS

The application is a continuation-in-part application of U.S. patent application Ser. No. 15/489,705, titled "Method and Apparatus for Rapid Sterilization of a Room", filed Apr. 17, 2017, the contents of which is hereby incorporated by reference, which is a continuation-in-part application of U.S. Pat. No. 9,623,131, titled "Method and Apparatus for Rapid Sterilization of Hazmat Suits, Surgical Instruments and the Like", filed Oct. 29, 2015, the contents of which is hereby incorporated by reference, which claims the benefit of the filing date of U.S. Provisional Patent Application Ser. No. 62/072,306, filed on Oct. 29, 2014, entitled "Method and Apparatus for Rapid Sterilization of Hazmat Suits, Surgical Instruments and the Like," the entire disclosure of which is hereby incorporated by reference into the present disclosure.

II. BACKGROUND

There is recurrent need for rapid sterilization of materials and tools exposed to hazardous infectious agents such as Ebola and other harmful bacteria and pathogens. What is proposed is the equivalent of an air shower for persons entering a cleanroom, but in this case it is a rapid, highly efficient means for the sterilization of the surface of exposed hazmat suits while the person is wearing the suit. In the case of surgical instruments, the rapid sterilization is accomplished in a scaled down version of the system disclosed. In other embodiments, the light shower may be used for the disinfection and sterilization of a room, such as a hospital room. An embodiment of the invention is illustrated in the appended figures.

III. SUMMARY

In one respect, disclosed is an apparatus for sterilizing a room comprising: a laser configured to emit a pulsed laser beam; and a robotic arm configured to direct the pulsed laser beam to a scattering optical element and to change the position of the scattering optical element; wherein the scattering optical element is configured to substantially isotropically scatter the radiation of the pulsed laser beam to sterilize the room.

In another respect, disclosed is a method for sterilizing a room comprising: using a laser to generate a pulsed laser beam; using a robotic arm to direct the pulsed laser beam to a scattering optical element and to change the position of the scattering optical element; and using the scattering optical element to substantially isotropically scatter the radiation of the pulsed laser beam to sterilize the room.

Numerous additional embodiments are also possible.

IV. BACKGROUND

There is recurrent need for rapid sterilization of materials and tools exposed to hazardous infectious agents such as Ebola and other harmful bacteria and pathogens. What is proposed is the equivalent of an air shower for persons entering a cleanroom, but in this case it is a rapid, highly efficient means for the sterilization of the surface of exposed hazmat suits while the person is wearing the suit. In the case of surgical instruments, the rapid sterilization is accomplished in a scaled down version of the system disclosed. In other embodiments, the light shower may be used for the disinfection and sterilization of a room, such as a hospital room. An embodiment of the invention is illustrated in the appended figures.

V. BRIEF DESCRIPTION OF THE DRAWINGS

Other objects and advantages of the invention may become apparent upon reading the detailed description and upon reference to the accompanying drawings.

Figure 1:
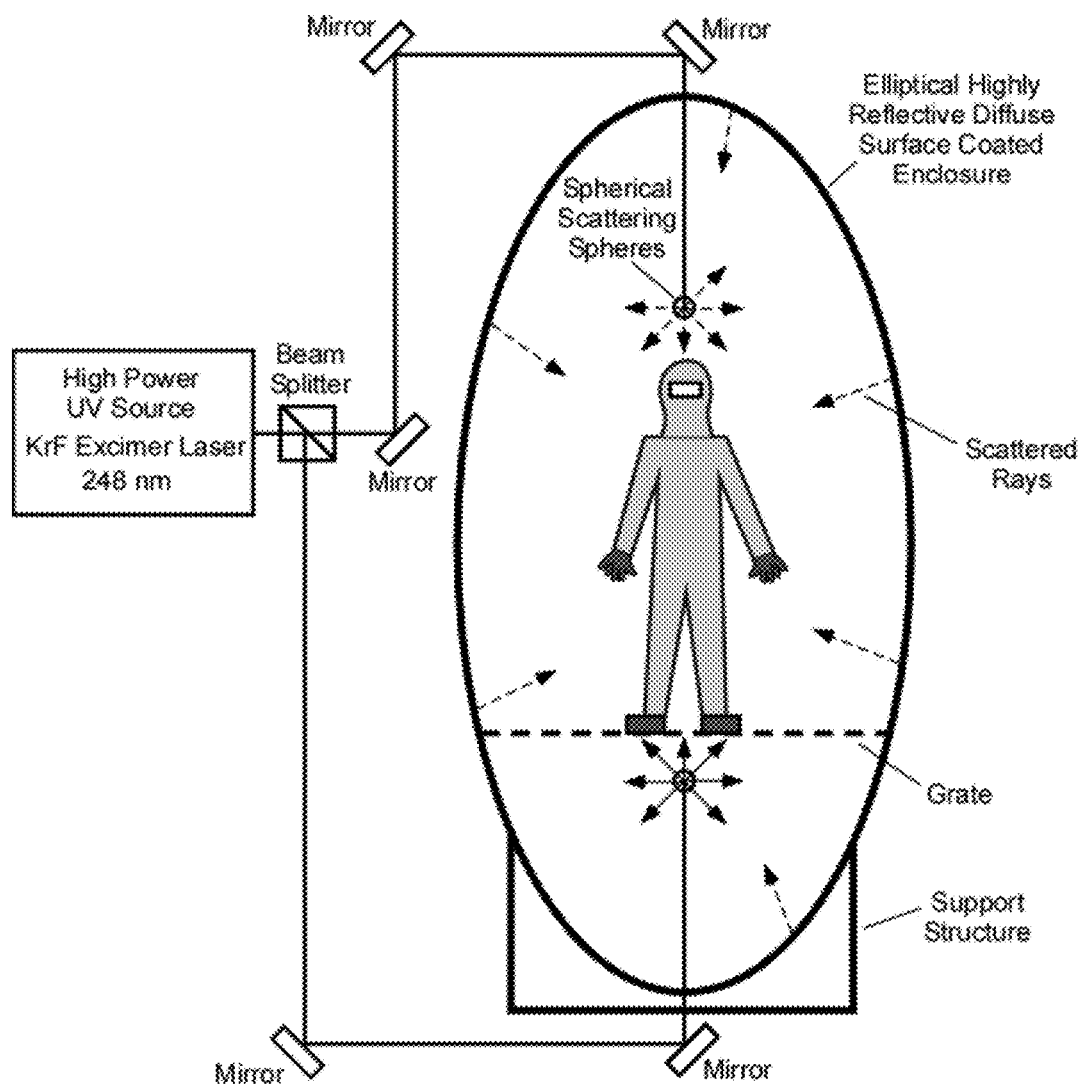
FIG. 1 is a schematic diagram illustrating a rapid sterilizer, in accordance with some embodiments.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

VI. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

Referring to FIG. 1, an embodiment has a high power Excimer laser using KrF pump media emitting nanosecond UV light pulses at 248 nm. This pulsed UV light has very efficient antibiotic characteristics. The beam from this laser source is split into two beams by a beam splitter (BS) shown in FIG. 1. These beams are steered by means of mirrors (M) to two substantially isotropically scattering optical element, such as spherically scattering spheres, located at the foci of an ellipsoidal highly reflecting diffuse surface coated enclosure. Because the UV light pulses are brought into spherically scattering sources at the foci of an ellipsoidal cavity, the entire cavity will be uniformly illuminated with the UV light pulses. A person (as shown in FIG. 1) will be instantly uniformly illuminated and the hazmat suit they are wearing will be rapidly sterilized and sanitized. To achieve proper centering of the person, a grate with wide open spacing is used as the floor in the enclosure. A support structure holds the enclosure with the major axis vertically. In other embodiments, the laser comprises a fourth harmonic q-switched Nd:YAG solid state laser, a fourth harmonic mode locked Nd:YAG solid state laser, a fourth harmonic q-switched Nd:YLF solid state laser, a fourth harmonic mode locked Nd:YLF solid state laser, a fourth harmonic q-switched Nd:YVO$_4$ solid state laser, and/or a fourth harmonic mode locked Nd:YVO$_4$ solid state laser. All of these laser sources are capable of generating short pulses of far UV light which maximizes the lethality of the radiation acting on the pathogenic organisms.

Figure 2:
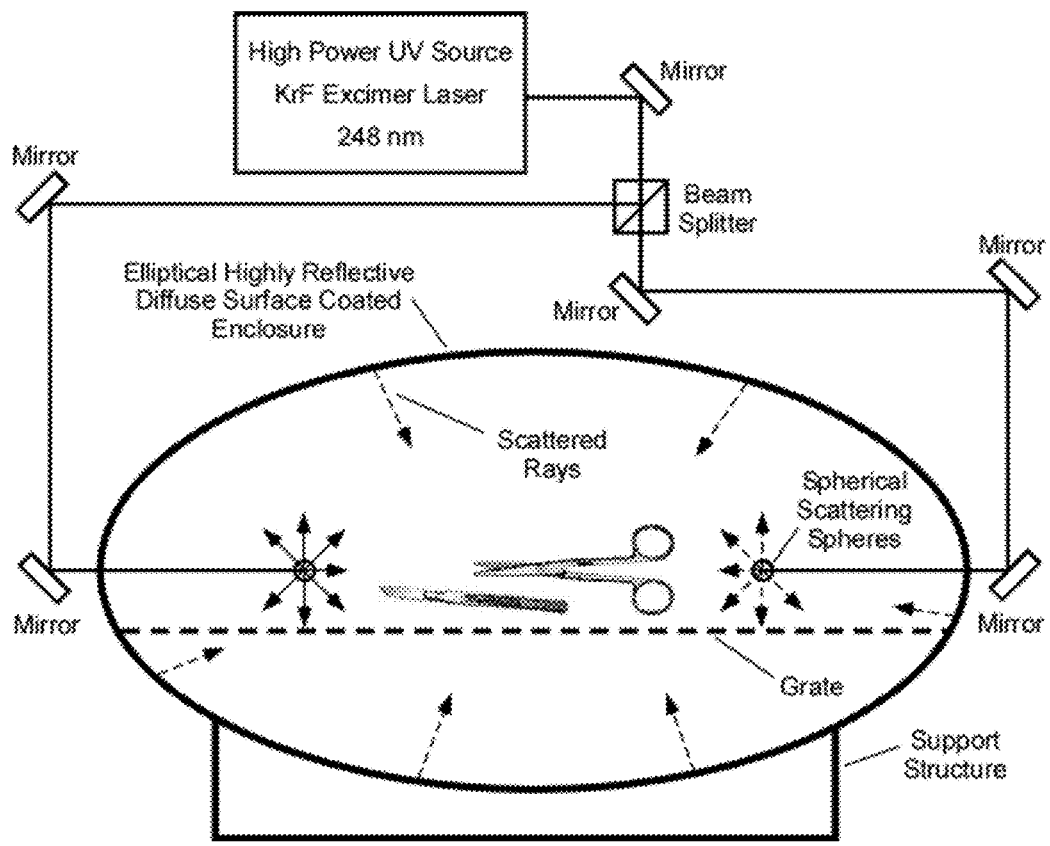
FIG. 2 is a schematic diagram illustrating a rapid sterilizer, in accordance with some embodiments.

A related embodiment is shown in FIG. 2. In this apparatus, a scaled down version of the above described system is shown. Again a high power KrF Excimer laser emitting nanosecond laser pulses at 248 nm is beam steered to two spherically scattering spheres located at the foci of a properly coated ellipsoidal enclosure as shown in FIG. 2. To be rapidly sterilized and sanitized, the surgical instruments, such as scalpels, forceps, and even endoscopes, are placed on a grate positioned near the major axis of the enclosure. In this arrangement, as in the above disclosed one, the sterilizing pulsed UV light uniformly illuminates the targeted objects placed near the major axis. A support structure as shown keeps the ellipsoidal enclosure horizontal.

Figure 3:
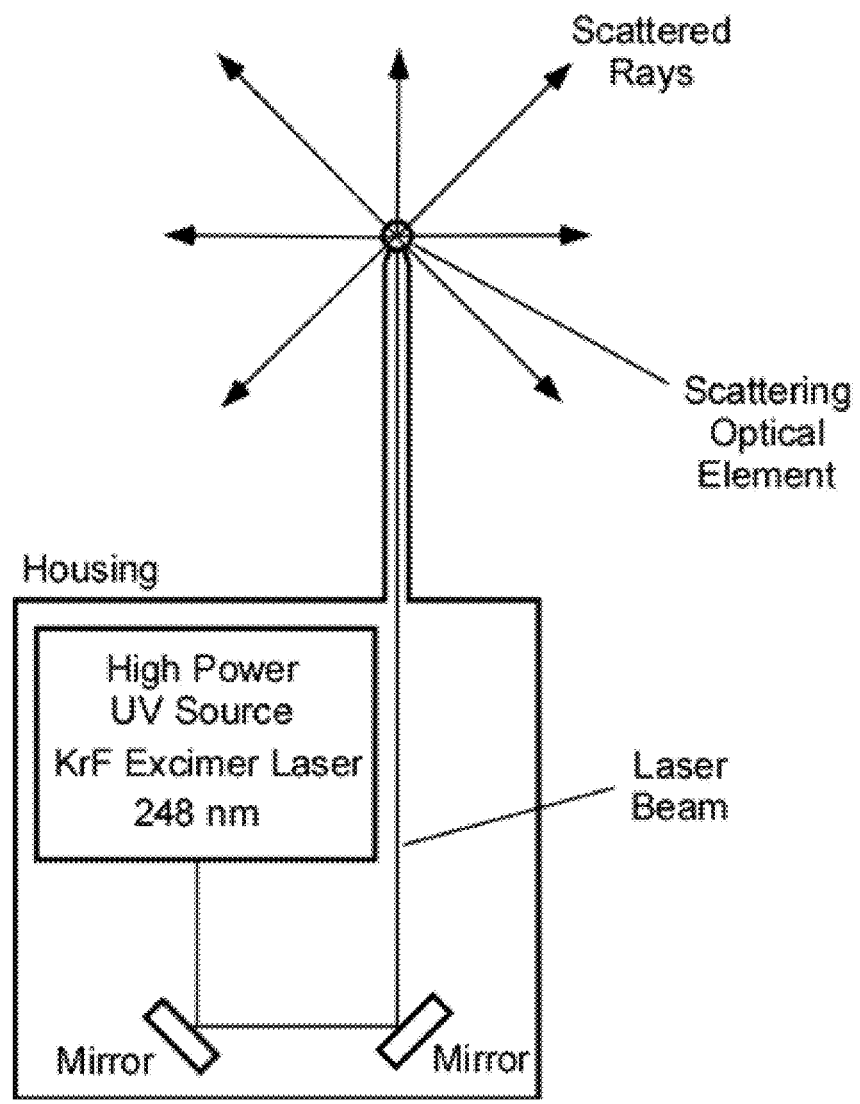
FIG. 3 is a schematic diagram illustrating a rapid sterilizer, in accordance with some embodiments.

In yet another related embodiment, shown in FIG. 3, the apparatus comprises a scattering optical element configured to scatter incident laser radiation external to a housing. A high power KrF Excimer laser emitting nanosecond laser pulses at 248 nm is beam steered with mirrors to a scattering optical element. Depending on the exact laser source, the wavelength may range from about 200 nm to about 320 nm and the pulsed laser beam may comprise nanosecond or picosecond light pulses. In some embodiments, the scattering optical element is a spherically scattering sphere which isotropically illuminates a room with sterilizing pulsed UV light to rapidly sterilize the room. The spherically scattering sphere comprises a hollow fused silica bulb filled with either solid or hollow fused silica spheres. In some embodiments, the fused silica bulb may be rotated. In an alternate embodiment, the scattering optical element comprises a fiber optic bundle, i.e., a fused bundle of individual fiber optic filaments. In this embodiment, the pulsed UV light is projected radially outward from the fiber optic bundle forming an omnidirectional, substantially planar sheet of UV light and in order to sterilize the entire room, the fiber optic bundle is rotated in a plane substantially orthogonal to the incident laser beam. An example of one such fiber optic bundle was disclosed in U.S. Pat. No. 5,898,809 issued to J. Taboada, et al., which is herein incorporated by reference.

An example embodiment of a spherically scattering sphere may be produced by filling a small fused silica hollow bulb with fused silica solid spheres of an appropriate dimension. The fused silica solid spheres scatter the incident laser radiation in a substantially isotropic manner.

Figure 4:
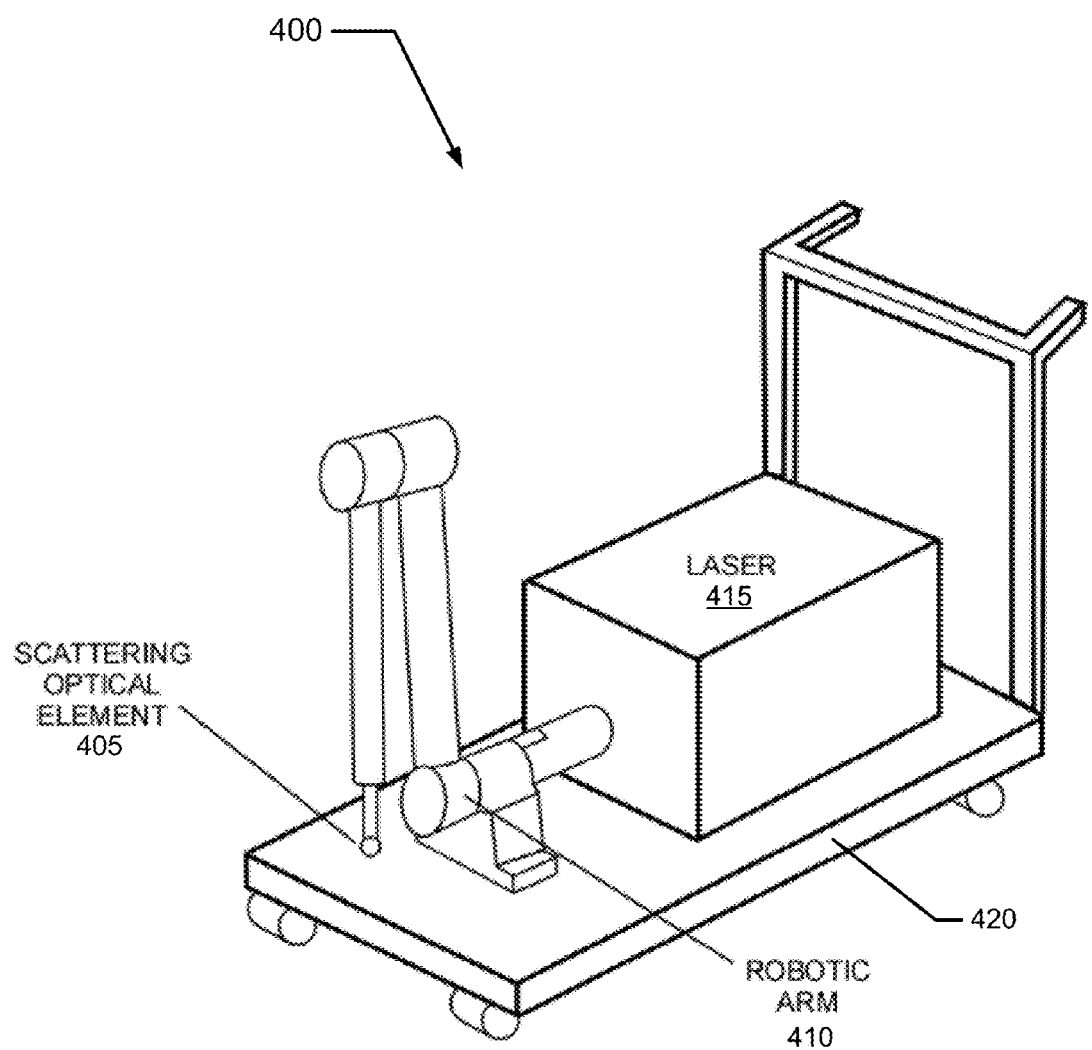
FIG. 4 is a schematic diagram illustrating a rapid sterilizer, in accordance with some embodiments.

In yet another related embodiment, shown in FIG. 4, the apparatus 400 comprises a scattering optical element 405 positioned at the end of a robotic arm 410 wherein the scattering optical element is configured to scatter incident laser radiation from a laser 415. The robotic arm is designed to move the scattering optical element to different positions in order to be able to get above, below, or behind obstructions or objects in a room that may prevent the thorough sterilization of a room. The robotic arm may have two or more degrees of freedom. One such laser is a high power KrF Excimer laser emitting nanosecond laser pulses at 248 nm. Depending on the exact laser source, the wavelength may range from about 200 nm to about 320 nm and the pulsed laser beam may comprise nanosecond or picosecond light pulses. In some embodiments, the scattering optical element is a spherically scattering sphere which isotropically illuminates a room with sterilizing pulsed UV light to rapidly sterilize the room. The spherically scattering sphere comprises a hollow fused silica bulb filled with either solid or hollow fused silica spheres. In some embodiments, the fused silica bulb may be rotated. In an alternate embodiment, the scattering optical element comprises a fiber optic bundle, i.e., a fused bundle of individual fiber optic filaments. In this embodiment, the pulsed UV light is projected radially outward from the fiber optic bundle forming an omnidirectional, substantially planar sheet of UV light and in order to sterilize the entire room, the fiber optic bundle is rotated in a plane substantially orthogonal to the incident laser beam. An example of one such fiber optic bundle was disclosed in U.S. Pat. No. 5,898,809 issued to J. Taboada, et al., which is herein incorporated by reference.

In some embodiment, the apparatus 400 is mounted onto a movable platform 420. In such an embodiment, the sterilizing laser system may be transported to different areas and rooms that are in need of sterilization.

An example embodiment of a spherically scattering sphere may be produced by filling a small fused silica hollow bulb with fused silica solid spheres of an appropriate dimension. The fused silica solid spheres scatter the incident laser radiation in a substantially isotropic manner.

In alternate embodiments, other UV sterilization light sources may be used, such as placing xenon or mercury vapor lamps at the end of the robotic arm.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

The invention claimed is:

1. An apparatus for sterilizing a room comprising:
   a laser configured to emit a pulsed laser beam; and
   a robotic arm configured to direct the pulsed laser beam to a scattering optical element and to change the position of the scattering optical element;
   wherein the scattering optical element is configured to substantially isotropically scatter the radiation of the pulsed laser beam to sterilize the room.

2. The apparatus of claim 1, wherein the laser comprises at least one of a KrF Excimer laser, a fourth harmonic q-switched Nd:YAG solid state laser, a fourth harmonic mode locked Nd:YAG solid state laser, a fourth harmonic q-switched Nd:YLF solid state laser, a fourth harmonic mode locked Nd:YLF solid state laser, a fourth harmonic q-switched Nd:YVO$_4$ solid state laser, and a fourth harmonic mode locked Nd:YVO$_4$ solid state laser.

3. The apparatus of claim 1, wherein the robotic arm comprises two or more degrees of freedom.

4. The apparatus of claim 1, wherein the pulsed laser beam comprises a wavelength ranging between about 200 nm to about 320 nm.

5. The apparatus of claim 1, wherein the pulsed laser beam comprises nanosecond or picosecond light pulses.

6. The apparatus of claim 1, wherein the scattering optical element comprises a hollow fused silica bulb filled with fused silica spheres.

7. The apparatus of claim 6, wherein the fused silica spheres are solid.

8. The apparatus of claim 6, wherein the fused silica spheres are hollow.

9. The apparatus of claim 1, wherein the scattering optical element comprises a fiber optic bundle.

10. The apparatus of claim 9, wherein the fiber optic bundle is configured to be rotated about a plane substantially orthogonal to the intercepted pulsed laser beam.

11. A method for sterilizing a room comprising:
using a laser to generate a pulsed laser beam;
using a robotic arm to direct the pulsed laser beam to a scattering optical element and to change the position of the scattering optical element; and
using the scattering optical element to substantially isotropically scatter the radiation of the pulsed laser beam to sterilize the room.

12. The method of claim 11, wherein the laser comprises at least one of a KrF Excimer laser, a fourth harmonic q-switched Nd:YAG solid state laser, a fourth harmonic mode locked Nd:YAG solid state laser, a fourth harmonic q-switched Nd:YLF solid state laser, a fourth harmonic mode locked Nd:YLF solid state laser, a fourth harmonic q-switched Nd:YVO$_4$ solid state laser, and a fourth harmonic mode locked Nd:YVO$_4$ solid state laser.

13. The method of claim 11, wherein the robotic arm comprises two or more degrees of freedom.

14. The method of claim 11, wherein the pulsed laser beam comprises a wavelength ranging between about 200 nm to about 320 nm.

15. The method of claim 11, wherein the pulsed laser beam comprises nanosecond or picosecond light pulses.

16. The method of claim 11, wherein the substantially isotropically scattering optical element comprises a hollow fused silica bulb filled with fused silica spheres.

17. The method of claim 16, wherein the fused silica spheres are solid.

18. The method of claim 16, wherein the fused silica spheres are hollow.

19. The method of claim 11, wherein the scattering optical element comprises a fiber optic bundle.

20. The method of claim 19, further comprising rotating the fiber optic bundle in a plane substantially orthogonal to the intercepted pulsed laser beam.

* * * * *